United States Patent [19]

Ishii et al.

[11] Patent Number: 5,654,474
[45] Date of Patent: Aug. 5, 1997

[54] AROMATIC DIISOCYANATE AND METHOD OF PRODUCING THE SAME

[75] Inventors: Michie Ishii; Amane Mochizuki, both of Osaka, Japan

[73] Assignee: Nitto Denko Corporation, Osaka, Japan

[21] Appl. No.: 723,878

[22] Filed: Sep. 23, 1996

[30] Foreign Application Priority Data

Sep. 29, 1995 [JP] Japan .................................. 7-276518

[51] Int. Cl.$^6$ ................................................. C07C 263/04
[52] U.S. Cl. ........................ 560/359; 560/338; 560/345
[58] Field of Search ................................ 560/345, 338, 560/359

[56] References Cited

U.S. PATENT DOCUMENTS 4,017,459  4/1977  Onder ........................................ 260/47

FOREIGN PATENT DOCUMENTS 1-132553  5/1989  Japan ........................... C07C 119/048

OTHER PUBLICATIONS

"Conversion of Isocyanates to Carbodiimides Catalyst Studies", John J. Monagle, Nov., 1962.
"A Simple, Convienient, and Efficient Method for the Synthesis of Isocyanates from Urethanes", J. Org. Chem. 1995, 60, 257–258.
"A New Synthesis of Isocyanates and Isothiocyanates", Angew. Chem. internat. Edit/vol. 7(1968)/No. 12.

*Primary Examiner*—Samuel Barts
*Attorney, Agent, or Firm*—Sughrue, Mion, Zinn, Macpeak & Seas

[57] ABSTRACT

Novel aromatic diisocyanate and a method of producing the same. The method comprises reacting a diamine compound with a chloroformate to produce an urethane intermediate, and then reacting the urethane intermediate with a halogenated organosilicon compound or a halogenated organoboron compound, using an organic solvent capable of dissolving both the diamine compound and the urethane intermediate. This method enables to produce the aromatic diisocyanate by one-pot. The aromatic diisocyanate has excellent various properties such as high heat resistance and chemical resistance.

6 Claims, 1 Drawing Sheet

AROMATIC DIISOCYANATE AND METHOD OF PRODUCING THE SAME

SUMMARY OF THE INVENTION

The present invention relates to a novel aromatic diisocyanate and a new method of producing the aromatic diisocyanate.

A polymer which forms moldings having excellent various properties such as high heat resistance, chemical resistance, etc., can be obtained by polymerizing the aromatic diisocyanate of the present invention.

BACKGROUND OF THE INVENTION

Aromatic diisocyanates are raw materials of many useful polymers such as aromatic polyurethanes, aromatic polyamides, aromatic polyimides, aromatic polyureas, aromatic polycarbodiimides, etc.

In these aromatic diisocyanates, a compound which is somewhat structurally relevant to the compound of the present invention is a compound represented by following formula (6) disclosed in JP-A-1-132553 (the term "JP-A" as used herein means an "unexamined published Japanese patent application"):

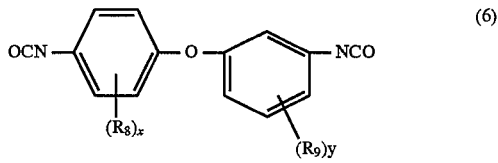

wherein $R_8$ and $R_9$ each represent a lower alkyl group having from 1 to 4 carbon atoms or a halogen atom, and x and y each represent an integer of from 1 to 4.

Further, U.S. Pat. No. 4,017,459 discloses in Example 12 an aromatic diisocyanate represented by following formula (7):

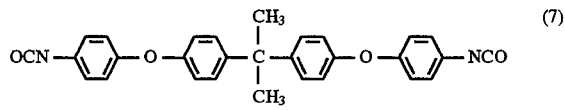

However, these aromatic diisocyanate compounds greatly differ from the compound of the present invention represented by formula (1) described hereinbelow in the chemical structure. Further, since polymers which use these conventional aromatic diisocyanates as the raw materials generally have high melting point, melt molding of these polymers is difficult or film forming from these polymer solutions is difficult because they have low solubility to organic solvents. Also, it may be in general difficult to produce polymers having high degree of polymerization using these aromatic diisocyanates. To obtain mechanical properties suitable for films and moldings, divalent aromatic residues in a polymer skeleton must be para-linked. However, such a polymer skeleton has the disadvantage that the skeleton has a rigidity and also has a poor flexibility. Further, since such an aromatic diisocyanate has a low melting point and a poor crystalline property, there are problems that the isolation and purification thereof are difficult and even when the aromatic diisocyanate is obtained as a solid, the diisocyanate is easily hydrolyzed into an aromatic diamine. Accordingly, there is a problem that when a polymerization reaction is carried out using such an aromatic diisocyanate as a monomer, a high polymer may not be obtained or a side-reaction may occur.

SUMMARY OF THE INVENTION

As a result of various investigations on an aromatic polymer having an excellent moldability together with a heat resistance and giving films and moldings having an excellent flexibility and a high performance, it has been found that the polymer satisfying the above-described requirements can be obtained by polymerizing as a monomer a diisocyanate which has a p-phenylene skeleton and four aromatic rings in the molecule, each aromatic ring being bonded each other with an ether bond or a hexafluoroisopropylidene bond. The present invention has been attained based on this finding.

According to a first embodiment of the present invention, there is provided an aromatic diisocyanate represented by following formula (1):

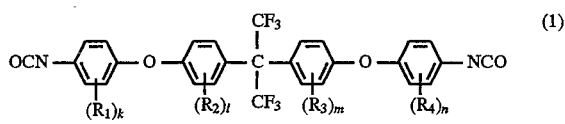

wherein $R_1$, $R_2$, $R_3$, and $R_4$, which may be the same or different, each independently represent a lower alkyl group having from 1 to 4 carbon atoms (e.g., methyl, ethyl, isopropyl, and butyl) or a halogen atom (e.g., chlorine, bromine, and fluorine), and k, l, m, and n each represent an integer of from 0 to 4, which shows the number of substituent(s).

According to a second embodiment of the present invention, there is provided a method of producing the aromatic diisocyanate represented by the formula (1) described above, which comprises reacting a diamine compound represented by following formula (3):

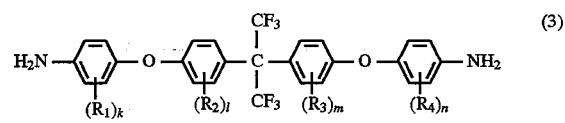

wherein $R_1$, $R_2$, $R_3$, and $R_4$ each independently represent a lower alkyl group having from 1 to 4 carbon atoms or a halogen atom, and k, l, m, and n each represent an integer of from 0 to 4, with chloroformate in the presence of a basic compound to produce an urethane intermediate, and reacting the urethane intermediate thus obtained with a halogenated organosilicon compound or a halogenated organoboron compound, wherein an organic solvent capable of dissolving both the diamine compound and the urethane intermediate is used and the aromatic diisocyanate is produced by a one-pot.

DETAILED DESCRIPTION OF THE INVENTION

Figure 1:
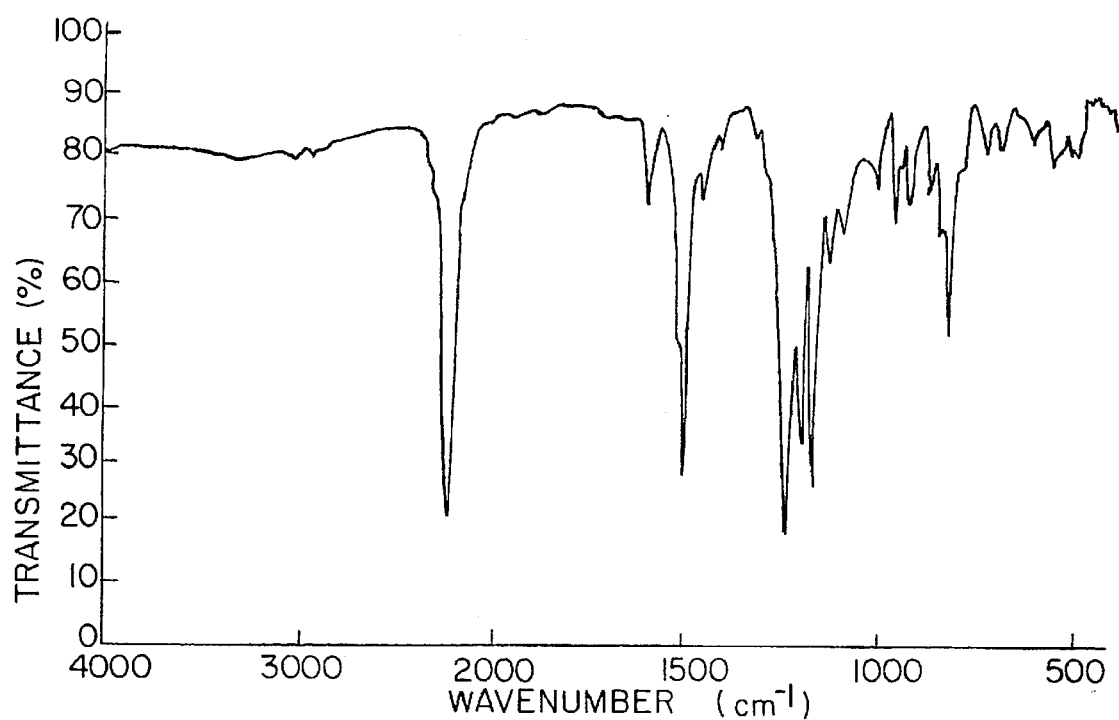
FIGS. 1 and 2 are IR spectra of the materials produced in Example 1 and 4 respectively.

The present invention is described in detail below.

The aromatic diisocyanate of the present invention represented by the formula (1) described above is a novel compound.

In the formula (1), k, l, m, and n each represent an integer of from 0 to 4. Usually, those are 0 or 1. In particular, the aromatic diisocyanate represented by following formula (2) having no substituent is particularly preferred as the aromatic diisocyanate of the present invention.

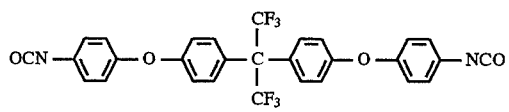

$$\text{OCN}-\langle\bigcirc\rangle-\text{O}-\langle\bigcirc\rangle-\underset{\underset{\text{CF}_3}{|}}{\overset{\overset{\text{CF}_3}{|}}{\text{C}}}-\langle\bigcirc\rangle-\text{O}-\langle\bigcirc\rangle-\text{NCO} \quad (2)$$

On the other hand, in producing the aromatic diisocyanate represented by the formula (1) having two or more substituents on the phenylene rings, the aromatic diamine compound represented by the formula (3) described above is used as the raw material. However, such an aromatic diamine compound is not generally commercially available.

Hitherto, it is known that aromatic diisocyanates such as diphenylmethane diisocyanate (MDI), or tolylene diisocyanate (TDI) are useful as monomers of various aromatic polyamides and aromatic polycarbodiimides, and the synthesis methods, the polymers, the characteristic data are described in many literatures. However, the compound of the present invention, 2,2-bis[4-(4-isocyanato(substituted) phenoxy)phenyl]hexafluoropropane, is a novel aromatic diisocyanate, and there are no reports about the characteristic values, etc., of the compound.

The aromatic diisocyanate according to the present invention includes the above-described 2,2-bis[4-(4-isocyanatophenoxy)phenyl]hexafluoropropane(BAPF-NCO)having no substituent on each phenyl group, and the alkyl or halogen substituted products thereof.

The aromatic diisocyanate compound of the present invention can be synthesized by isocyanating the corresponding diamine compound, which is a precursor of the diisocyanate compound, by the conventional method. Examples of such a diamine compound are 2,2-bis[4-(4-aminophenoxy)phenyl]hexafluoropropane (BAPF) and the alkyl or halogen substituted products thereof (e.g., HFBAPP, trade name, made by Wakayama Seika Kogyo K.K., BIS-AF-A, trade name, made by Central Glass Co., Ltd., etc.).

The method of isocyanating such a diamine compound is, for example, a method of reacting the diamine compound with phosgene, diphenyl carbonate, or carbonyl diimidazole. Further, an urethane compound may be produced from the diamine compound using a halogenated alkyl or an aryl formate followed by isolating and purifying the urethane compound. The urethane compound may be dissolved in a solvent, and then isocyanated by a method of using chlorosilane as a catalyst (G. Greber, et. al., *Angew. Chem. Int. Ed.*, Vol. 17, No. 12, 941(1968)) or a method of using catechol borane (V. L. K. Valli. et. al., *Journal of Organic Chemistry*, Vol., 60, 257(1995)). Other method which may be used is a method of using a carboxylic acid such as 2,2 -[bis-(4-carboxyphenoxy)phenyl]hexafluoropropane as a precursor of the diisocyanate and isocyanating the carboxylic acid by a Curtius decomposition.

Efficient and novel production method for producing the novel aromatic diisocyanate of the present invention is explained below, The production method of the present invention is a method of producing the aromatic diisocyanate represented by the formula (1) described above, comprising reacting a diamine compound represented by the formula (3) described above with chloroformate in the presence of a basic compound to produce an urethane intermediate, and reacting the urethane intermediate thus obtained with a halogenated organosilicon compound or a halogenated organoboron compound, wherein an organic solvent capable of dissolving both the diamine compound and the urethane intermediate is used and the aromatic diisocyanate is produced by a one-pot.

The term "producing by one-pot" used herein means a synthetic method that at least 2 steps of reactions are conducted in one reaction vessel. That is, the one-pot production intended in the present invention means that an urethane compound is produced as an intermediate using a diamine compound as the raw material, and without isolating and purifying the urethane intermediate, the subsequent isocyanation is conducted, in one reaction vessel, thereby the desired diisocyanate compound is obtained.

This one-pot production can prevent loss of the raw material due to isolation and purification, shorten the production steps, improve the yield of the desired final product, and insure safety of the work.

According to the method of the present invention, the diamine compound is reacted with chloroformate in the presence of a basic compound using a solvent capable of dissolving both the diamine compound and the urethane intermediate, and the urethane intermediate is then reacted with a halogenated organosilicon compound or a halogenated organoboron compound to conduct isocyanation of the urethane intermediate, whereby the desired final product can be obtained. The above reactions all are conducted in one reaction vessel.

The organic solvent used in the reaction can be any solvent so long as it can dissolve both the diamine compound and the urethane intermediate. Examples of such a solvent are ether compounds such as tetrahydrofuran (THF), diethyl ether, or dioxane; ketone compounds such as acetone, or methyl ethyl ketone; ester compounds such as ethyl acetate; hydrocarbon compounds such as toluene, xylene, or benzene; and halogenated hydrocarbon compounds such as chloroform, or methylene chloride. These solvents may be used alone or as mixtures thereof.

The concentration of the diamine compound in the reaction solution is from 1 to 50% by weight, preferably from 5 to 40% by weight, and more preferably from 10 to 30% by weight, based on the weight of the reaction solution. If the concentration of the diamine compound is too low, a long time is required for the reaction, which is not practical. If the concentration is too high, undesirable side reactions may occur.

An organic base or an inorganic base can be used as the basic compound in either case of using the organic halogenated silicon compound or the organic halogenated boron compound, which is used in the subsequent reaction. However, the organic base is more suitable in the point that it is easily dissolved in a solvent. Further, of the organic bases, a tertiary amine such as triethylamine, or pyridine is suitable in the point that it does not hinder the reaction. A primary amine and a secondary amine are not preferred since these amines each have active hydrogen and those may react with the aromatic diisocyanate formed.

The amount of the basic compound used is from 3.0 to 8.0 times, and preferably from 3.5 to 7.2 times, the mole number of the diamine compound. The basic compound may be added by dividing the amount used. However, it is preferred that the basic compound be present from the beginning of the reaction.

First, an urethane compound as an intermediate is synthesized by reacting the diamine compound with chloroformate. Examples of the chloroformate which can be used include methyl chloroformate, ethyl chloroformate, phenyl chloroformate, and p-nitrophenyl chloroformate. In these chloroformates, phenyl chloroformate or p-nitrophenyl chloroformate is more suitable in order to obtain a sufficiently activated urethane intermediate for obtaining the isocyanate.

The amount of the chloroformate used is preferably from 2.0 to 2.4 times the mole number of the diamine compound.

The reaction temperature for obtaining the urethane intermediate is from −40° C. to 70° C., preferably from −20° C. to 50° C., and more preferably from 0° C. to 30° C. If the reaction temperature is lower than −40° C., the reaction is difficult to proceed, while the reaction temperature is higher than 70° C., a side reaction such as a condensation may occur.

The isocyanation is successively conducted in the same reaction vessel without isolating the urethane intermediate thus formed. A catalyst is used in the reaction for obtaining the isocyanate from the urethane intermediate, and examples thereof which can be used include a halogenated organosilicon compound and a halogenated organoboron compound.

The halogenated organosilicon compound preferably used is a compound represented by following formula (4):

$$SiR_5R_6R_7X \quad (4)$$

wherein $R_5$, $R_6$, and $R_7$ each independently represent a lower alkyl group having from 1 to 3 carbon atoms, an aryl group, an alkoxy group, or a halogen atom, and X represents a halogen atom.

In these halogenated organosilicon compounds, chlorosilanes such as trimethylchlorosilane, triethylchlorosilane, trimethoxychlorosilane, or tetrachlorosilane are preferred, and trimethylchlorosilane is more preferred from the standpoints of ease of handling and the cost.

The amount of the halogenated organosilicon compound used is from 2.0 to 4.0 times, and preferably from 2.2 to 3.6 times, the mole number of the urethane intermediate (bisurethane). If the amount used is too small, the unreacted raw material may remain, while if the amount used is too large, it may be difficult to remove the unreacted raw material after completion of the reaction, or an undesirable side reaction may occur.

When the halogenated organosilicon compound is used, the reaction temperature in proceeding the reaction for forming the isocyanate can appropriately be changed in the range of generally from −50° C. to 200° C., preferably from −10° C. to 150° C., and more preferably from 20° C. to 120° C. If the reaction temperature is too low, the reaction may not proceed, while if the reaction temperature is too high or the reaction mixture is heated too long, an undesirable side reaction may occur, or the product may decompose. Therefore, it is preferred to proceed the reaction by gradually increasing the temperature from a low temperature while tracing the reaction with, for example, infrared (IR) spectrum.

The halogenated organoboron compound which is preferably used is halogenated catechol boranes represented by following formula (5):

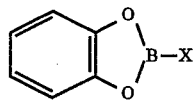

(5)

wherein X represents a halogen atom.

Examples of the halogenated catechol boranes include chlorocatechol borane, and bromocatechol borane. Chlorocatechol borane is suitable from the standpoints of ease of handling and the cost.

The halogenated catechol boranes have an activity to the thermal decomposition of urethane higher than that of chlorosilanes, Therefore, formates other than phenyl chloroformate can also be used as the reaction reagent in obtaining the urethane intermediate.

The amount of the halogenated organoboron compound used is from 2.0 to 4.0 times, and preferably from 2.2 to 3.6 times, the mole number of the urethane intermediate (bisurethane). If the amount used is too small, unreacted raw materials may remain, while if the amount used is too large, it may be difficult to remove unreacted raw materials after completion of the reaction, or an undesirable side reaction may occur.

When the halogenated organoboron compound is used, the reaction temperature in proceeding the isocyanation is generally from −50° C. to 150° C., preferably from −30° C. to 100° C., and more preferably from −10° C. to 50° C. The reaction temperature can appropriately be changed according to the combination of the diamine compound, chloroformate, and the halogenated organoboron compound used. If the reaction temperature is too low, the reaction may not proceed, while if the reaction temperature is too high, an undesirable side reaction may occur, or the product formed may decompose. Therefore, it is preferred to proceed the reaction by gradually increasing the temperature from a low temperature while tracing the reaction with TLC (thin-layer chromatography) or the IR (infrared) spectrum.

After completion of the reaction, the isocyanate formed can be isolated and purified. That is, after removing hydrochlorides formed by the reaction and the excess reaction reagents, the product can be purified by a flash column, a re-crystallization, a distillation, etc., according to the properties of the product.

By measuring the melting point of the compound obtained, and also by the mass spectrum and the IR spectrum of the compound, the compound obtained is identified as the aromatic diisocyanate represented by the formula (I) described above.

The aromatic diisocyanate of the present invention is a high crystalline solid and can be preserved for a long period of time at room temperature. The aromatic diisocyanate of the present invention can be used as a monomer for polymerization to produce a polymer such as polycarbodiimide, polyurethane, or polyimide.

A polymer obtained using the aromatic diisocyanate of the present invention as the monomer for polymerization, for example, an aromatic polycarbodiimide obtained by condensing the monomer in the presence of a phosphorus catalyst by the conventional method (J .J. Monagle, Journal of Organic Chemistry, 27, 3851(1962)), has excellent solubility toward wide range of solvents, and films having a high performance may be cast from the polymer solution. It is believed that those excellent properties are due to, for example, that the aromatic polycarbodiimide has a rigid p-phenylene skeleton in the molecular structure and contains fluorine atoms. That is, the polymer synthesized using the aromatic diisocyanate represented by the formula (I) has a high heat resistance because of its rigid structure. Further, fluorine atoms are present, so that the polarity increases and the solubility is improved. Therefore, it is easy to obtain the polymer having a relatively high degree of polymerization and the polymer obtained is excellent in the solution moldability. In addition, moldings having a high performance can be obtained.

According to the one-pot production method of the aromatic diisocyanate of the present invention, it is possible to prevent loss of the raw materials due to the isolation and purification of the product, shorten the production steps, improve the yield for the desired final product, and insure safety of the work.

The present invention is described in more detail by reference to the following examples, but it should be understood that the invention is not construed as being limited thereto.

EXAMPLE 1

A 50 ml two-necked flask equipped with a dropping funnel was charged with 2.00 g (3.86 mmoles) of 2,2-bis[4-(4-aminophenoxy)phenyl]hexafluoropropane (BAPF), 20 ml of toluene, and 2.10 ml (15 mmoles) of triethylamine. 1.21 ml (7.72 mmoles) of phenyl chloroformate was introduced into the dropping funnel and the reaction vessel (flask) was cooled to 0° C. by an ice-bath. Phenyl chloroformate was added dropwise over 10 minutes, and the resulting mixture was stirred for 30 minutes while returning the temperature to room temperature. 0.87 g (7.72mmoles) of trimethylchlorosilane was added thereto at room temperature and the mixture was stirred for 10 minutes. When the reaction temperature was gradually raised to 80° C. and the mixture was stirred at 80° C. for 3 hours, isocyanation proceeded. The product obtained was purified by a conventional method to obtain 1.83 g (yield 83%) of white solids.

The compound obtained had a melting point of 137° C. Molecular ion peak of M+=570 was observed in mass spectrum, and absorption of a carbonyl group of an isocyanate was observed at 2,260 cm$^{-1}$ in IR spectrum (see FIG. 1). Hitachi 80A (trade name, manufactured by Hitachi, Ltd.) was used to measure the mass spectrum, and IR-810 (trade name, manufactured by Nippon Bunko Kogyo K. K.) was used to measure the IR spectrum.

Accordingly, it was confirmed that the product was 2,2-bis[4-(4-isocyanatophenoxy)phenyl]hexafluoropropane (BAPF-NCO).

EXAMPLE 2

A 50 ml two-necked flask equipped with a dropping funnel was charged with 0.88 g (1.7 mmoles) of 2,2-bis[4-(4-aminophenoxy)phenyl]hexafluoropropane (BAPF), 10 ml of methylene chloride, and 1.4 ml (10 mmoles) of triethylamine.

0.53 g (3.4 mmoles) of phenyl chloroformate was introduced into the dropping funnel and the reaction vessel (flask) was cooled to 0° C. by an ice-bath. Phenyl chloroformate was added dropwise to the mixture over 10 minute, and the mixture was stirred for 30 minutes while returning the temperature to room temperature. The mixture was ice-cooled again, 0.76 g (4.9 mmoles) of chlorocatechol borane was added thereto, and the resulting mixture was stirred for 50 minutes. When the reaction temperature was raised to room temperature and the mixture was stirred for one hour, isocyanation proceeded to obtain 0.55 g (yield 57%) of white solids.

The compound obtained had a melting point of 137° C. Similar to Example 1, molecular ion peak of M+=570 was observed in the mass spectrum, and absorption of a carbonyl group of an isocyanate was observed at 2,260 cm$^{-1}$ in the IR spectrum. Accordingly, it was confirmed that the product obtained was 2,2-bis[4-(4-isocyanatophenoxy)phenyl]hexafluoropropane (BAPF-NCO).

EXAMPLE 3

One liter three-necked flask equipped with a dropping funnel was charged with 20 g (38.6 mmoles) of 2,2-bis[4-(4-aminophenoxy)phenyl]hexafluoropropane (BAPF), 200 ml of THF, and 13.2 ml (94.3 mmoles) of triethylamine. 13.2 ml (84 mmoles) of phenyl chloroformate was introduced into the dropping funnel and the reaction vessel (flask) was cooled to 0° C. by an ice-bath. Phenyl chloroformate was added dropwise to the mixture over 15 minutes, and the mixture was stirred for 30 minutes while returning the temperature to 0° C. A salt formed was hydrolyzed with 100 ml of water and extracted with chloroform. The organic layer formed was collected and dried with anhydrous magnesium sulfate. The solvent was distilled off and the residue formed was recrystallized from toluene to obtain 22.2 g (yield 76%) of white solids.

20 g (26.0 mmoles) of the urethane obtained as the white solids was charged in a one liter three-necked flask equipped with a dropping funnel together with 170 ml of methylene chloride and 11.0 ml (78.6 mmoles) of triethylamine. Further, 5.65 g (52 mmoles) of trimethylchlorosilane was charged in the dripping funnel, and added dropwise to the mixture in the flask over 5 minutes. 170 ml of toluene was further added thereto. Methylene chloride was distilled off and the mixture was stirred for 4 hours while gradually raising the temperature to 120° C. The mixture was further stirred at 120° C. for 2 hours. Salts formed were removed by filtration, and the filtrate was concentrated by an evaporator. The reaction mixture obtained was purified by a flash column to obtain 7.3 g (yield 49%) of white solids.

The compound obtained had a melting point of 137° C. Molecular ion peak of M+=570 was observed in the mass spectrum, and absorption of the carbonyl group of an isocyanate was observed at 2,260 cm$^{-1}$ in the IR spectrum. Accordingly, it was confirmed that the product was 2,2-bis[4-(4-isocyanatophenoxy)phenyl]hexafluoropropane (BAPF-NCO).

EXAMPLE 4

Figure 2:
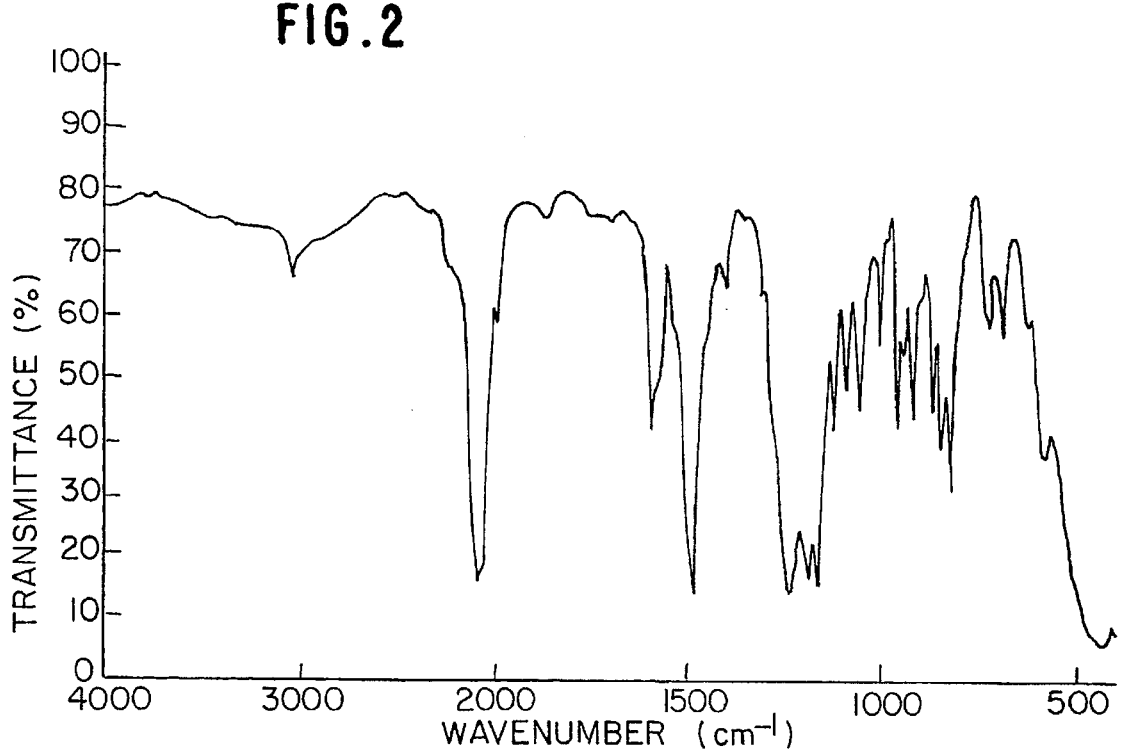

Into an eggplant-shaped flask (100 ml) were charged 5 g of the isocyanate compound (BAPF-NCO) obtained in Example 1, 25 ml of THF, and 0.0135 g of a carbodiimidation catalyst (1-phenyl-3-methylphospholene oxide). The resulting mixture was stirred at 60° C. for 6.5 hours to obtain a polycarbodiimide resin having Mn=7,000. The IR spectrum of the resin is shown in FIG. 2.

The resin was cast on a glass plate and dried at 90° C. for 30 minutes to obtain a film. The film had a heat curing temperature higher than 400° C., and had a flexibility even when the film was subjected to a heat treatment at 250° C. for one hour.

COMPARATIVE EXAMPLE 1

2,2-Bis[4-(4-isocyanatophenoxy)phenyl]propane (BAPP-NCO) was synthesized according to the method described in U.S. Pat. No. 4,017,569 as follows.

To 10.25 g of 2,2-bis(4-aminophenoxyphenyl)propane (BAPP) was added dropwise 200 ml of chlorobenzene containing a saturated amount of phosgene while ice-cooling at a temperature of 10° C. or less over 30 minutes. After completion of the addition, the temperature of the reaction solution was raised to 100° C. over 4 hours, and the reaction was further carried out at 130° C. for 2 hours. After cooling the reaction mixture to room temperature, the product was extracted with petroleum ether and cooled to -5° C. to obtain 3.5% (yield 30%) of the desired crystals. The melting point of the product was from 63° C. to 65° C. It was confirmed that the product was 2,2-bis[4-(4-isocyanatophenoxy)phenyl]propane (BAPP-NCO].

When the BAPP-NCO was allowed to stand at room temperature, hydrolysis proceeded gradually. Thus, the product was poor in stability.

While the invention has been described in detail and with reference to specific embodiments thereof, it will be apparent to one skilled in the art that various changes and modifications can be made therein without departing from the spirit and scope thereof.

What is claimed is:

1. An aromatic diisocyanate represented by following formula (1);

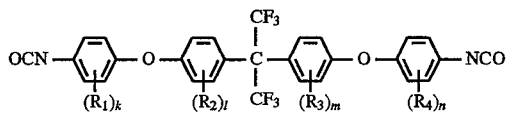

wherein $R_1$, $R_2$, $R_3$, and $R_4$ each independently represent a lower alkyl group having from 1 to 4 carbon atoms or a halogen atom, and k, l, m, and n each represent an integer of from 0 to 4.

2. The aromatic diisocyanate of claim 1, wherein the aromatic diisocyanate is represented by following formula (2);

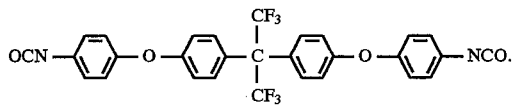

3. A method of producing an aromatic diisocyanate represented by following formula (1);

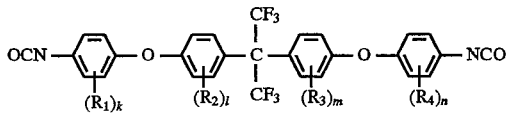

wherein $R_1$, $R_2$, $R_3$, and $R_4$ each independently represent a lower alkyl group having from 1 to 4 carbon atoms or a halogen atom, and k, l, m, and n each represent an integer of from 0 to 4, which comprises reacting a diamine compound represented by following formula (3):

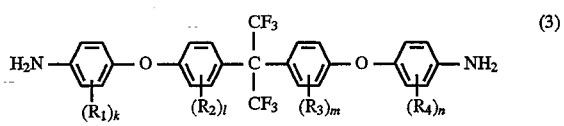

wherein $R_1$, $R_2$, $R_3$, and $R_4$ each independently represent a lower alkyl group having from 1 to 4 carbon atoms or a halogen atom, and k, l, m, and n each represent an integer of from 0 to 4, with a chloroformate in the presence of a basic compound to produce a urethane intermediate, and reacting the urethane intermediate with a compound selected from the group consisting of a halogenated organo-silicon compound and a halogenated organoboron compound, wherein an organic solvent capable of dissolving both the diamine compound and the urethane intermediate is used, and the aromatic diisocyanate is produced by one-pot.

4. The method of producing an aromatic diisocyanate of claim 3, wherein the halogenated organosilicon compound is a compound represented by following formula (4);

wherein $R_5$, $R_6$, and $R_7$ each independently represent an alkyl group, an aryl group, an alkoxy group, or a halogen atom, and X represents a halogen atom.

5. The method of producing an aromatic diisocyanate of claim 3, wherein the halogenated organoboron compound is a compound represented by following formula (5);

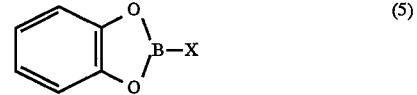

wherein X represents a halogen atom.

6. The method of producing an aromatic diisocyanate of claim 3, wherein the basic compound is a tertiary amine.

* * * * *